US006815165B2

(12) United States Patent
Lee et al.

(10) Patent No.: US 6,815,165 B2

(45) Date of Patent: Nov. 9, 2004

(54) **METHOD FOR IDENTIFYING *MYCOBACTERIUM TUBERCULOSIS* AND MYCOBACTERIA OTHER THAN TUBERCULOSIS, TOGETHER WITH DETECTING RESISTANCE TO AN ANTITUBERCULOSIS DRUG OF MYCOBACTERIA OBTAINED BY MUTATION OF RPOB GENE**

(75) Inventors: Hyeyoung Lee, No. 190-1106, Woosung Apartment, Yangjae-1-dong, Seocho-ku, Seoul 137-793 (KR); Hye Eun Bang, Seoul (KR); Sang-Nae Cho, No. 111-602, Hansin Apartment, 929, Mok-6-dong, Yangchon-ku, Seoul 158-759 (KR); Gill-Han Bai, Seongnam-shi (KR); Sang-Jae Kim, Seoul (KR)

(73) Assignees: Sang-Nae Cho, Seoul (KR); Hyeyoung Lee, Kangwon-Do (KR)

( * ) Notice: Subject to any disclaimer, the term of this patent is extended or adjusted under 35 U.S.C. 154(b) by 0 days.

(21) Appl. No.: 10/058,422

(22) Filed: Jan. 30, 2002

(65) Prior Publication Data

US 2003/0108881 A1 Jun. 12, 2003

(30) Foreign Application Priority Data

Jul. 19, 2001 (KR) ........................................ 2001-43450

(51) Int. Cl.[7] .......................... C12Q 1/68; C12P 19/34; C07H 21/02; C07H 21/04

(52) U.S. Cl. .......................... 435/6; 435/91.2; 435/810; 536/22.1; 536/24.33

(58) Field of Search .......................... 435/6, 91.2, 810; 536/22.1, 24.33, 24.3, 24.32

(56) References Cited

FOREIGN PATENT DOCUMENTS

WO 01/31061 * 5/2001 ............ C12Q/1/68

OTHER PUBLICATIONS

Hayward, A.C., et al., "Typing of mycobacteria using spoligotyping," *Thorax* , *53*:329–330 (1998).

Ruiz, M., et al., "Application of molecular biology techniques to the diagnosis of nontuberculous mycobacterial infections," *APMIS, 109*(*12*), 857–864 (2001).

Domenech, P., et al., "Restriction fragment length polymorphisms of 16S rRNA genes in the differentiation of fast–growing mycobacterial species," *FEMS Microbiol. Letters, 116*, 19–24 (1994).

Takewaki, S–I., et al., "Nucleotide Sequence Comparison of the Mycobacterial dnaJ Gene and PCR–Restriction Fragment Length Polymorphism Analysis for Identification of Mycobacterial Species," *Int. J. Syst. Bacteriol., 44*, 159–166 (1994).

Taylor, T.B., "Routine Use of PCR–Restriction Fragment Length Polymorphism Analysis for Identification of Mycobacteria Growing in Liquid Media," *J. Clin. Microbiol., 35*, 79–85 (1997.

Wong, D. A., et al., "Simple and Rational Approach to the Identification of *Mycobacterium tuberculosis, Mycobacterium avium* Complex Species, and Other Commonly Isolated Mycrobacteria," *J. Clin. Microbiol.*, 39, 3768–3771 (2001).

Brunello, F., "Identification of 54 Mycobacterial Species by PCR–Restriction Fragment Length Polymorphism Analysis of the hsp65 Gene," *J. Clin. Microbiol., 39*, 2799–2806 (2001).

Miller, N., et al., "Evaluation of the LiPA Mycobacteria Assay for Identification of MYCOBACTERIAl Species for BACTEC 12B Bottles," *J. Clin. Microbiol., 38*, 1915–1919 (2000).

Roth, A., et al., "Novel Diagnostic Algorithm for Identification of Mycobacteria Using Genus–Specific Amplification of the 16S–23S rRNA Gene Spacer and Restriction Endonucleases," *J. Clin. Microbiol., 38*, 1094–1104 (2000).

Horsburgh, C., "Epidemiology of Disease Caused by Nontuberculous Mycobacteria," *Seminars in Respir. Infect., 11*, 244–251 (1996).

Devallois, A., et al., "Rapid Identification of Mycobacteria to Species Level by PCR–Restriction Fragment Length Polymorphism Analysis of the hsp65 Gene and Proposition of an Algorithm To Differentiate 34 Mycobacterial Species," *J. Clin. Microbiol.*, 35, 2969–2973 (1997).

Suffys, P. N., et al., "Rapid Identification of Mycobacteria to the Species Level Using INNO–LiPA Mycobacteria, a Reverse Hybridization Assay," *J. Clin. Microbiol., 39*, 4477–4482 (2001).

Kox, L. F.F., et al., "PCR Assay Based on DNA Coding for 16S rRNA for Detection and Identification of Mycobacteria in Clinical Samples, "*J. Clin. Microbiol* 33: 3225–3233 (1995).

Sanguinetti, M., et al., "Routine Use of PCR–Reverse Cross–Blot Hybridization Assay for Rapid Identification of *Mycobacterium* Species Growing in Liquid Media,"*J Clin Microbiol* 36: 1530–1533 (1998).

Garcia, M. J., et al., "Separation of *Mycobacterium gadium* from Other Rapidly Growing Mycobacteria on the Basis of DNA Homology and Restriction Endonuclease Analysis," *J. Gen. Microbiol.* 132: 2265–2269 (1986).

Patel, R., et al., "Isolation and Restriction Endonuclease Analysis of Mycobacterial DNA,". *J. Gen. Microbiol.* 132: 541–551 (1986).

(List continued on next page.)

*Primary Examiner*—Kenneth R. Horlick
*Assistant Examiner*—Joyce Tung
(74) *Attorney, Agent, or Firm*—Nixon & Vanderhye P.C.

(57) ABSTRACT

The present invention provides a method for identifying *Mycobacterium tuberculosis* and non-tuberculosis Mycobacterium (MOTT), and for the determination of drug susceptibility of *M. tuberculosis* based on detection of mutations in the rpoB gene.

6 Claims, 7 Drawing Sheets

OTHER PUBLICATIONS

Lee, H., et al., "Species Identification of Mycobacteria by PCR–Restriction Fragment Length Polymorphism of the *rpo*B Gene," *J. Clin. Microbiol.* 38: 2966–2971 (2000).

Kamerbeek, J., et al., "Simultaneous Detection and Strain Differentiation of *Mycobacterium tuberculosis* for Diagnosis and Epidemiology," *J. Clin. Microbiol.* 35:907–914 (1997).

Woods, G. L., et al., "Mycobacteria Other than *Mycobacterium tuberculosis*: Review of Microbiologic and Clinical Aspects," *Rev. Infect. Dis.* 9(2): 275–294 (1987).

Jenkins, P. A., "Mycobacteria in the environment," *J. Appl. Bact. Sym. Suppl.* 70: 137S–141S (1991).

Tsukamura, M., et al., "Epidemologic Studies of Lung Disease Due to Mycobacteria Other than *Mycobacterium tuberculosis* in Japan, " *Rev. Infect. Dis.* 3(5): 997–1007 (1981).

O'Brien, R. J., et al., "The Epidemiology of Nontuberculous Mycobacterial Diseases in the United States. Results from a National Survey," *Am. Rev. Respir. Dis.* 135: 1007–1014 (1987).

Gai, G.H. et al., "Clinically Isolated Mycobacteria other than *Mycobacterium tuberculosis* from 1980 to 1990 in Korea," *J. Kor. Soc. Microbiol.* 28(1): 1–5 (1993).

Bai, G.H., "Rapid Identification of *Mycobacterium avium* and *Mycobacterium intracellulare* by the Amplification of rRNA Sequences," *J. Kor. Soc. Microbiol.* 27(5): 443–448 (1992).

* cited by examiner

*rpoB* gene *of M. tuberculosis*

Total: 531 bp tca aggagaagcg ctacgacctg gcccgcgtcg gtcgctataa (43)
ggtcaacaag aagctcgggc tgcatgtcgg cgagcccatc acgtcgtcga cgctgaccga (103)
agaagacgtc gtggccacca tcgaatatct ggtccgcttg cacgagggtc agaccacgat (163)
gaccgttccg ggcggcgtcg aggtgccggt ggaaaccgac gacatcgacc acttcggcaa (223)
ccgccgcctg cgtacggtcg gcgagctgat ccaaaaccag atccgggtcg gcatgtcgcg (283)
gatggagcgg gtggtccggg agcggatgac cacccaggac gtggaggcga tcacaccgca (343)
gacgttgatc aacatccggc cggtggtcgc cgcgatcaag gagttcttcg gcaccag*cca* (403)
*gctgagccaa ttcatggacc agaacaaccc gctgtcgggg ttgacccaca agcgccgact* (463)
*gtcggcgctg ggg*cccggcg gtctgtcacg tgagcgtgcc gggctggagg tccgcgacgt (523)
gcacccgt Underlined Letters: Primer-binding regions

Bold Letters: polymorphic region existing in *M. tuberculosis* and MOTTs

*Italic letters*: the region related to the resistance against rifampin

FIGURE 2

SEQUENCE LISTING

```
<160> NUMBER OF SEQ ID NOS: 31

<210> SEQ ID NO 1
<211> LENGTH: 25
<212> TYPE: DNA
<213> ORGANISM: Artificial Sequence
<220> FEATURE:
<223> OTHER INFORMATION: MOTT-rpo-long-B-5' primer for PCR
      amplication of rpoB gene

<400> SEQUENCE: 1

tcaaggagaa gcgctacgac ctggc                                          25


<210> SEQ ID NO 2
<211> LENGTH: 24
<212> TYPE: DNA
<213> ORGANISM: Artificial Sequence
<220> FEATURE:
<223> OTHER INFORMATION: TR8-long-NB-3' primer for PCR
      amplication of rpoB gene

<400> SEQUENCE: 2

acgggtgcac gtcgcggacc tcca                                           24


<210> SEQ ID NO 3
<211> LENGTH: 20
<212> TYPE: DNA
<213> ORGANISM: Artificial Sequence
<220> FEATURE:
<223> OTHER INFORMATION: Oligomer probe for all types of Mycobacteria

<400> SEQUENCE: 3

gacgtcgtcg ccaccatcga                                                20


<210> SEQ ID NO 4
<211> LENGTH: 15
<212> TYPE: DNA
<213> ORGANISM: Artificial Sequence
<220> FEATURE:
<223> OTHER INFORMATION: Oligomer probe for M. tuberculosis complex
```

-continued

<400> SEQUENCE: 4
catgtcggcg agccc 15

<210> SEQ ID NO 5
<211> LENGTH: 19
<212> TYPE: DNA
<213> ORGANISM: Artificial Sequence
<220> FEATURE:
<223> OTHER INFORMATION: Oligomer probe for M. avium

<400> SEQUENCE: 5
aaacggtgag ccgatcacc 19

<210> SEQ ID NO 6
<211> LENGTH: 18
<212> TYPE: DNA
<213> ORGANISM: Artificial Sequence
<220> FEATURE:
<223> OTHER INFORMATION: Oligomer probe for M. intracellularae

<400> SEQUENCE: 6
aaacctgcac gcgggcga 18

<210> SEQ ID NO 7
<211> LENGTH: 21
<212> TYPE: DNA
<213> ORGANISM: Artificial Sequence
<220> FEATURE:
<223> OTHER INFORMATION: Oligomer probe for M. scrofulaceum

<400> SEQUENCE: 7
aaaaacgtac ggatggccag c 21

<210> SEQ ID NO 8
<211> LENGTH: 19
<212> TYPE: DNA
<213> ORGANISM: Artificial Sequence
<220> FEATURE:
<223> OTHER INFORMATION: Oligomer probe for M. kansasii type I + V

<400> SEQUENCE: 8
aaaggccacg atgaccgtg 19

<210> SEQ ID NO 9
<211> LENGTH: 21
<212> TYPE: DNA
<213> ORGANISM: Artificial Sequence
<220> FEATURE:
<223> OTHER INFORMATION: Oligomer probe for M. kansasii type II + III + IV

<400> SEQUENCE: 9
aaaaatctca ggatggccag c 21

<210> SEQ ID NO 10
<211> LENGTH: 21
<212> TYPE: DNA
<213> ORGANISM: Artificial Sequence
<220> FEATURE:
<223> OTHER INFORMATION: Oligomer probe for M. gastri

<400> SEQUENCE: 10
aaaaatctca gggtggccag g 21

<210> SEQ ID NO 11

-continued

<211> LENGTH: 16
<212> TYPE: DNA
<213> ORGANISM: Artificial Sequence
<220> FEATURE:
<223> OTHER INFORMATION: Oligomer probe for M. fortuitum complex

<400> SEQUENCE: 11
cctgaacgcc ggccag 16

<210> SEQ ID NO 12
<211> LENGTH: 16
<212> TYPE: DNA
<213> ORGANISM: Artificial Sequence
<220> FEATURE:
<223> OTHER INFORMATION: Oligomer probe for M. peregrinum

<400> SEQUENCE: 12
gttccggtcg aggtgg 16

<210> SEQ ID NO 13
<211> LENGTH: 20
<212> TYPE: DNA
<213> ORGANISM: Artificial Sequence
<220> FEATURE:
<223> OTHER INFORMATION: Oligomer probe for M. chelonae

<400> SEQUENCE: 13
aaatggtgac tgccaccacg 20

<210> SEQ ID NO 14
<211> LENGTH: 20
<212> TYPE: DNA
<213> ORGANISM: Artificial Sequence
<220> FEATURE:
<223> OTHER INFORMATION: Oligomer probe for M. abscesus

<400> SEQUENCE: 14
aaaaggtgac caccaccacc 20

<210> SEQ ID NO 15
<211> LENGTH: 15
<212> TYPE: DNA
<213> ORGANISM: Artificial Sequence
<220> FEATURE:
<223> OTHER INFORMATION: Oligomer probe for M. ulcerans

<400> SEQUENCE: 15
ggccagccca tcacc 15

<210> SEQ ID NO 16
<211> LENGTH: 16
<212> TYPE: DNA
<213> ORGANISM: Artificial Sequence
<220> FEATURE:
<223> OTHER INFORMATION: Oligomer probe for M. genavanse/M. simiae

<400> SEQUENCE: 16
ccagccgacg atgacg 16

<210> SEQ ID NO 17
<211> LENGTH: 19
<212> TYPE: DNA
<213> ORGANISM: Artificial Sequence
<220> FEATURE:
<223> OTHER INFORMATION: Oligomer probe for M. gordonae type I, III, IV

<400> SEQUENCE: 17

-continued aaagtcggcg atccgatca 19

<210> SEQ ID NO 18
<211> LENGTH: 19
<212> TYPE: DNA
<213> ORGANISM: Artificial Sequence
<220> FEATURE:
<223> OTHER INFORMATION: Oligomer probe for M. gordonae type II

<400> SEQUENCE: 18
aaaaacgtcg gcaagccga 19

<210> SEQ ID NO 19
<211> LENGTH: 19
<212> TYPE: DNA
<213> ORGANISM: Artificial Sequence
<220> FEATURE:
<223> OTHER INFORMATION: Oligomer probe for M. szulgai

<400> SEQUENCE: 19
aaatctgaac gtcggcgag 19

<210> SEQ ID NO 20
<211> LENGTH: 19
<212> TYPE: DNA
<213> ORGANISM: Artificial Sequence
<220> FEATURE:
<223> OTHER INFORMATION: Oligomer probe for M. terrae

<400> SEQUENCE: 20
aaagctcagg acggtcagt 19

<210> SEQ ID NO 21
<211> LENGTH: 18
<212> TYPE: DNA
<213> ORGANISM: Artificial Sequence
<220> FEATURE:
<223> OTHER INFORMATION: Oligomer probe for Wild Type 509-514

<400> SEQUENCE: 21
aaccagctga gccaattc 18

<210> SEQ ID NO 22
<211> LENGTH: 18
<212> TYPE: DNA
<213> ORGANISM: Artificial Sequence
<220> FEATURE:
<223> OTHER INFORMATION: Oligomer probe for M. Wild Type 515-520

<400> SEQUENCE: 22
atggaccaga acaacccg 18

<210> SEQ ID NO 23
<211> LENGTH: 18
<212> TYPE: DNA
<213> ORGANISM: Artificial Sequence
<220> FEATURE:
<223> OTHER INFORMATION: Oligomer probe for Wild Type 521-525

<400> SEQUENCE: 23
aaactgtcgg ggttgacc 18

<210> SEQ ID NO 24
<211> LENGTH: 18
<212> TYPE: DNA

-continued

<213> ORGANISM: Artificial Sequence
<220> FEATURE:
<223> OTHER INFORMATION: Oligomer probe for Wild Type 524-529

<400> SEQUENCE: 24
ttgacccaca agcgccga 18

<210> SEQ ID NO 25
<211> LENGTH: 16
<212> TYPE: DNA
<213> ORGANISM: Artificial Sequence
<220> FEATURE:
<223> OTHER INFORMATION: Oligomer probe for Wild Type 530-534

<400> SEQUENCE: 25
ctgtcggcgc tggggc 16

<210> SEQ ID NO 26
<211> LENGTH: 16
<212> TYPE: DNA
<213> ORGANISM: Artificial Sequence
<220> FEATURE:
<223> OTHER INFORMATION: Oligomer probe for Mutant Type 531TTG

<400> SEQUENCE: 26
ctgttggcgc tggggc 16

<210> SEQ ID NO 27
<211> LENGTH: 18
<212> TYPE: DNA
<213> ORGANISM: Artificial Sequence
<220> FEATURE:
<223> OTHER INFORMATION: Oligomer probe for Mutant Type 526 AAC

<400> SEQUENCE: 27
aaaaccaaca agcgccga 18

<210> SEQ ID NO 28
<211> LENGTH: 19
<212> TYPE: DNA
<213> ORGANISM: Artificial Sequence
<220> FEATURE:
<223> OTHER INFORMATION: Oligomer probe for Mutant Type 516 GTC

<400> SEQUENCE: 28
aatggtccag aacaacccg 19

<210> SEQ ID NO 29
<211> LENGTH: 18
<212> TYPE: DNA
<213> ORGANISM: Artificial Sequence
<220> FEATURE:
<223> OTHER INFORMATION: Oligomer probe for Mutant Type 513 CCA

<400> SEQUENCE: 29
aaagctgacc ccattcat 18

<210> SEQ ID NO 30
<211> LENGTH: 18
<212> TYPE: DNA
<213> ORGANISM: Artificial Sequence
<220> FEATURE:
<223> OTHER INFORMATION: Oligomer probe for Mutant Type 511CCG

<400> SEQUENCE: 30
aaagccgagc ccattcat 18

-continued

```
<210> SEQ ID NO 31
<211> LENGTH: 531
<212> TYPE: DNA
<213> ORGANISM: Artificial Sequence
<220> FEATURE:
<223> OTHER INFORMATION: Nucleotide sequence of the 531bp fragment
      obtained by PCR amplification of the rpoB gene of M. tuberculosis

<400> SEQUENCE: 31

tcaaggagaa gcgctacgac ctggcccgcg tcggtcgcta taaggtcaac aagaagctcg     60

ggctgcatgt cggcgagccc atcacgtcgt cgacgctgac cgaagaagac gtcgtggcca    120

ccatcgaata tctggtccgc ttgcacgagg gtcagaccac gatgaccgtt ccgggcggcg    180

tcgaggtgcc ggtggaaacc gacgacatcg accacttcgg caaccgccgc ctgcgtacgg    240

tcggcgagct gatccaaaac cagatccggg tcggcatgtc gcggatggag cgggtggtcc    300

gggagcggat gaccacccag gacgtggagg cgatcacacc gcagacgttg atcaacatcc    360

ggccggtggt cgccgcgatc aaggagttct tcggcaccag ccagctgagc caattcatgg    420

accagaacaa cccgctgtcg gggttgaccc acaagcgccg actgtcggcg ctggggcccg    480

gcggtctgtc acgtgagcgt gccgggctgg aggtccgcga cgtgcacccg t             531
```

METHOD FOR IDENTIFYING *MYCOBACTERIUM TUBERCULOSIS* AND MYCOBACTERIA OTHER THAN TUBERCULOSIS, TOGETHER WITH DETECTING RESISTANCE TO AN ANTITUBERCULOSIS DRUG OF MYCOBACTERIA OBTAINED BY MUTATION OF RPOB GENE

BACKGROUND OF THE INVENTION

This application claims priority to the foreign application KR 2001-43450 filed Jul. 19, 2001.

FIELD OF THE INVENTION

The present invention relates to a method for identifying *Mycobacterium tuberculosis* (hereinafter, referred to as '*M. tuberculosis*') and *Mycobacterium* Other Than Tuberculosis (hereinafter, referred to as 'MOTT'), and for the determination of resistance of *M. tuberculosis* to an antituberculosis drug obtained by the mutation of the rpoB gene.

DESCRIPTION OF THE RELATED ARTS

Tuberculosis is a chronic wasting disease caused by *M. tuberculosis*. Worldwide, it ranks the first in mortality and morbidity among infectious diseases (Global Tuberculosis Programme. Global Tuberculosis Control, WHO Report 1997. World Health Organization, 1997). Carriers of *M. tuberculosis* presently number about 1.9 billion, a third of the world population, and about 8–10 million of these carriers develop into new tuberculosis patients per year, and about 3 million of patients die of tuberculosis per year (Dolin P. J., Raviglion M. C., Kochi, A. (1994) Global tuberculosis incidence and mortality during 1990–2000. Bull World Health Organization. 72(2): 213–220; Kochi, A. (1992) The global tuberculosis situation and the new control strategy of the World Health Organization. *Tubercle*. SCI. 72:1-6; Styblo K. Epidemiology of Tuberculosis the Hague, Royal Netherland Tuberculosis Association (1991), p. 83 in: Minister of Health and Welfare, The Korean National Tuberculosis Association. Measures for Tuberculosis Control in 2000s, p5, 1997). Also, about a half of the population in Korea are carriers of *M. tuberculosis*, and about 150,000 persons develop into new tuberculosis patients per year, and about 14,000 patients per year die of tuberculosis (Sreevatsan S. Stockbauer K E, Pan X, Kreiswirth B N, Mogha S L, Jacobs W R Jr, Telenti A, Musser J M. (1997) Ethambutol resistance in *M. tuberculosis*: critical role of embB mutations. *Antimicrob Agents Chemother* 41:1677–1681).

Recently, it was reported that patients doubly infected with HIV virus and *M. tuberculosis* are much more susceptible to tuberculosis. The seriousness of the problem of tuberculosis has become increasingly apparent, together with the increase of HIV in the world as well. Presently, it is estimated that about 15 million patients are double infected by both the *M. tuberculosis* and HIV. Also, most of these patients will probably develop into fulminant tuberculosis patients, which will lead to their deaths (Narain J. P., Raviglione M. C., Kochi A. (1992) HIV-associated tuberculosis in developing countries: epidemiology and strategies for prevention. *Tuber Lung Dis*. SCI. 73(6): 311–321).

The insufficiency of the present antituberculosis drugs and improper treatment and control of tuberculosis in these developing countries results in the increase of patients with

*M. tuberculosis* which are the resistant to antituberculosis drugs (Global Tuberculosis Programme. Anti-tuberculosis drug resistance, WHO Report 1997. World Health Organization, 1997). The increasing appearance of resistant *M. tuberculosis* has resulted in the concomitant increase in tuberculosis related mortality and has obstructed attempts to eliminate it from a population (Ariel, P. M., M. C. Raiglion, A. Laszlo, N. Binkin, H. L. Rieder, F. Buster, D. L. Cohn, C. S. B. L. van weezenbeck, S. J. Kim, P. Chaulet, P. Nunn. (1998) Global surveillance for antituberculosis-drug resistance. *New England J. of Medicine*. SCI. 338:1641–1649; Centers for Disease Control. (1992) National action plan to combat multidrug-resistant tuberculosis. Morb Mortal Wkly Rep 41(RR-11):5–48; Global Tuberculosis Programme. Global project on Anti-tuberculosis Drug Resistance Surveillance. WHO Report 1997. World Health Organization, 1997; Tuberculosis: A Global Emergency (news). World Health Forum, 14(4):438, 1993. In: Minister of Health and Welfare, The Korean National Tuberculosis Association. Measures for Tuberculosis Control in 2000s, 1997). In the meantime, current treatment of resistant *M. tuberculosis* is quite costly and has low efficiency, thus the resistant mycobacteria often develops into incurable tuberculosis. Therefore, earlier diagnosis of resistant *M. tuberculosis* should result in more efficient treatment of tuberculosis patients.

In most countries, including Korea, the drug-susceptibility test for *M. tuberculosis* is performed using standard microbiological methods, which require long time periods of 8–10 weeks to grow *M. tuberculosis* in culture (Index of Korean Health and Welfare in 1996, p. 412, Korea Institute for Health and Social Affair, 1997). Therefore, methods for rapidly and accurately detecting the drug susceptibility of the infecting *M. tuberculosis* are needed. Rapid diagnosis of resistant mycobacteria may increase the efficiency of the tuberculosis treatment because it may provide proper treatment strategies earlier in the development of the disease. Ultimately, rapid diagnostic methods may slow the increase of incurable tuberculosis resulting from infection with drug-resistant *M. tuberculosis*. Therefore, such diagnostic methods are important health care technologies capable of decreasing further economic loss by prevention, elimination and treatment of tuberculosis.

Recently, the mechanism of drug-resistance was discovered by the use of genetic-based technology. For example, it is reported that the mechanism by which *M. tuberculosis* obtains resistance to rifampin, one of the strongest effective antituberculosis drugs, results from a nucleotide mutation in the 69bp region of the gene which encodes the β-subunit of RNA polymerase (rpoB gene) (Telenti A., Imboden P., Marchesi F., Lowrie D., Cole S., Colston M. J., Matter L., Schopfer K., Bodmer T. (1993) Detection of rifampicin-resistance mutation in *Mycobacterium tuberculosis. Lancet*. SCI. 341:647–50; Vareldzis B. P., Grosset J., de kantor I., Crofton J., Laszlo A., Felten M., Raviglione M. C., Kochi A. (1994) Drug-resistant Tuberculosis: Laboratory Issues, World Health Organization Recommendations. *Tuber Lung Dis*. SCI. 75(1):1–7). At least 97% of *M. tuberculosis* with resistance to rifampin is due to the above mutation.

The genus *Mycobacterium* includes, in addition to *M. tuberculosis, M. lepraeae* (Hansen's disease or Leprosy) and other *Mycobacterium* species generically called *Mycobacterium* Other Than Tuberculosis (hereinafter, referred to as 'MOTT'). MOTTs are mycobacteria which cause opportunistic infections, and thus MOTTs generally infect patients who have reduced immunity; however, normal persons can be infected on occasion. Since 1980, most of the industrialized nations have reported that MOTTs cause tuberculosis in HIV patients. Further, the number of diseases found to be caused by MOTTs has been increasing, so that the rapid and accurate identification of mycobacterial species has been recognized as being important for health care providers.

Conventional methods for identifying *M. tuberculosis* and MOTTs are based on various microbiological and biochemical properties of *Mycobacterium* species (Kochi A., Vareldzis B., Styblo K. (1993) Multidrug-resistant tuberculosis and its control. *Res Microbiol*. SCI. 144(2):104–110). However, such conventional identifications require for up to four weeks of growth time, depending on the types of mycobacteria, thus the identification time is prolonged. In addition, the results obtained by the conventional methods are sometimes unclear, and some *Mycobacterium* species cannot be distinguished from other species with these conventional methods. Therefore, to overcome the above problems of the conventional identifications, the identification of MOTTs using molecular biological methods has been recently developed.

Particularly, methods for the molecular biological identification of MOTTs using as its target, a highly conserved genetic domain in all mycobacterial species, were developed (Timpe A, Runyon E H: The relationship of "atypical" acid-fast bacteria to human disease: A preliminary report. *J Lab Clin Med.* 44: 202, 1954; Jenkins, P. A.: Lipid analysis for the identification of mycobacteria. *An appraisal. Rev. Infect. Dis.* 3: 382–866, 1981; Tsang, A., I. Drupa, M. Goldgerg, J. McClatchy, and P. Brennan. 1983. Use of serology and thin-layer chromatography for the assembly of an authenticated collection of serovars within the *Mycobacterium avium-Mycobacterium intracellulare-Mycobacterium scrofulaceum* complex. Int. J. Syst. Bacteriol.; Butler, W. R., K. C. Jost, Jr., and J. O. Kilburn. 1991. Identification of mycobacteria by high-performance liquid chromatography. J. Clin. Microbiol. 29:2468–2472, 33:285–292).

Among these, the rpoB gene found by the present inventors may be used in identifying MOTTs more simply and rapidly than the conventional molecular biological method using identification of the nucleotide polymorphism of 16S rRNA (KR99-46795).

That is to say, the rpoB gene includes highly conserved regions capable of being detected in all the species of mycobacteria. More importantly, the rpoB genes from Entero-bacteriaceae are not amplified by PCR using the primers based on the rpoB gene sequence of mycobacterial species, or if amplified, the PCR products are distinguishable from each other. Therefore, the mycobacterial rpoB gene may be used in preparation of PCR primers specific to *Mycobacterium* species.

Further, the results of the above prior studies by the present inventors show that the rpoB gene of *Mycobacterium* includes nucleotide regions having polymorphisms. Therefore, the rpoB gene may also be used in preparation of *Mycobacterium* species-specific probes for DNA-hybridization.

Conclusively, the present inventors found in prior studies that a 361bp region in the rpoB gene can be successfully used in the specific identification of *M. tuberculosis* and MOTTs.

SUMMARY OF THE INVENTION

An object of the present invention is to provide a method for specifically identifying *M. tuberculosis* and MOTTs, and to detect whether said mycobacteria has a mutation of the rpoB gene, rendering it drug resistant.

Another object of the present invention is to provide primers for PCR amplification of the rpoB gene used in identifying *M. tuberculosis* and MOTTs, and to detect the presence of the mutation of the rpoB gene.

Still another object of the present invention is to provide oligomer probes and a membrane to adhere said probes for performing reverse blot hybridization.

Yet another object of the present invention is to provide a kit for identifying *M. tuberculosis* and MOTTs, together with detecting the antimicrobial resistance of a mycobacterial species by detection of mutations of the rpoB gene, using oligomer probes adhered to the membrane and said primers, or which includes said primers, said oligomer probes and said membranes.

To achieve the above purposes, the present invention identifies *M. tuberculosis* and MOTTs, and detects whether the *Mycobacterium* has a mutation in the rpoB gene which would confer antibiotic resistance by the following method:

(1) isolating DNA from a sample;

(2) amplifying a 531bp fragment of the rpoB gene of the *Mycobacterium* by PCR using said mycobacterial DNA isolated in step (1) as template, and using the primers MOTT-rpo-long-B-5' (5'-TCAAGGAGAAGCGCTACGACCTGGC-3'; SEQ. ID. NO. 1) and TR8-long-NB-3'(5'-ACGGGTGCACGTCGCGGACCTCCA-3'; SEQ. ID. NO. 2); and, (3) performing PCR-reverse blot hybridization by hybridizing the PCR products obtained in step (2) to a membrane capable of adhering the oligomer probes of SEQ. ID. NOs. 3 to 30, wherein the oligomer probes of SEQ. ID. NOs. 3 to 20 are species-specific oligomer probes capable of binding to a specific DNA sequence of a specific mycobacterial species and wherein the oligomer probes of SEQ. ID. NOs. 21 to 30 are capable of hybridizing with specificity to mutants of the rpoB gene which confer drug resistance on *M. tuberculosis* or which are also capable of hybridizing to the wild type rpoB gene.

DETAILED DESCRIPTION OF THE INVENTION AND PREFERRED EMBODIMENTS

The present invention is explained in detail below.

In step (1), the samples are prepared from patients who are carriers or expected carriers of *M. tuberculosis*. Because the *Mycobacterium* infects the lungs, samples are preferably obtained from patient expectoration. The isolation of DNA from said samples may be performed by methods commonly known to a person skilled in the art.

In step (2), the primers MOTT-rpo-long-B-5' (SEQ ID NO. 1) and TR8-long-NB-3' (SEQ ID NO. 2) are used to amplify a 531bp fragment of the *Mycobacterium* rpoB gene by PCR, as illustrated in FIG. 1. As shown in FIG. 2, the 531bp PCR product includes i) a conserved sequence native to all *Mycobacterium*, ii) a species-specific polymorphic sequence, and iii) the sequence which, when mutated, confers drug resistance upon the host *M. tuberculosis*. Said amplified PCR product of the mycobacterial rpoB gene may be used to identify and distinguish between *M. tuberculosis* and MOTTs, and to detect a mutation in the rpoB gene. Such a mutation in the rpoB gene renders *M. tuberculosis* resistant to drugs such as rifampin, rifamycin, or derivatives thereof.

In step (3), the rpoB gene PCR product obtained in step (2) is hybridized with the oligomer probes of Table 1 below using the reverse blot hybridization method (Sambrook and Russell, Molecular Cloning: A laboratory manual, third edition, Cold Spring Harbor Press, New York, 2001). The oligomer probes of Table 1 below include oligomer probes that are capable of hybridizing with a specific DNA sequence of a specific species of *Mycobacterium*, and that are capable of hybridizing with specificity to the wild type rpoB gene or to mutated DNA sequences of the rpoB gene which confer resistance upon the host *M. tuberculosis* to drugs such as rifampin.

The oligomer probes described by SEQ ID NOs. 3 to 20 in Table 1 were constructed to hybridize with a specific DNA sequence of a specific species of *Mycobacterium*.

The oligomer probes WT1, WT2, WT3, WT4 and WT5 (SEQ ID NOs. 21–25) can be used to identify the wild type rpoB gene of *M. tuberculosis* by hybridizing with nucleotide sequences 509–514, 515–520, 521–529, 525–529 and 530–534, respectively, of the PCR product. The oligomer probes MT1, MT2, MT3, MT4 and MT5 (SEQ ID NOs. 26–30) can be used to detect mutations in the *M. tuberculosis* rpoB gene, specifically, TTG mutation of nucleotide 531, AAC mutation of nucleotide 526, GTC mutation of nucleotide 516, CCA mutation of nucleotide 516, and CCG mutation of nucleotide 511, respectively.

TABLE 1

| Name of Oligomer Probes | Sequence of Oligomer probe | Mycobacterium for targeting | SEQ ID NO. |
|---|---|---|---|
| MYC | GACGTCGTCGCCACCATCGA | All types of Mycobacteria | 3 |
| MTB | CATGTCGGCGAGCCC | *M. tuberculosis* complex | 4 |
| AVI | AAACGGTGAGCCGATCACC | *M. avium* | 5 |
| INT | AAACCTGCACGCGGGCGA | *M. intracellularae* | 6 |
| SCR | AAAAACGTACGGATGGCCAGC | *M. scrofulaceum* | 7 |
| KAN-I | AAAGGCCACGATGACCGTG | *M. kansasii* type I + V | 8 |
| KAN-II | AAAAATCTCAGGATGGCCAGC | *M. kansasii* type II + III + IV | 9 |
| GAS | AAAAATCTCAGGGTGGCCAGG | *M. gastri* | 10 |
| FOR-C | CCTGAACGCCGGCCAG | *M. fortuitum* complex | 11 |
| PER | GTTCCGGTCGAGGTGG | *M. peregrinum* | 12 |
| CHE | AAATGGTGACTGCCACCACG | *M. chelonae* | 13 |
| ABS | AAAAGGTGACCACCACCACC | *M. abscesus* | 14 |
| ULC | GGCCAGCCCATCACC | *M. ulcerans* | 15 |
| GEN/SIM | CCAGCCGACGATGACG | *M. genavanse*/*M. simiae* | 16 |
| GOR-I | AAAGTCGGCGATCCGATCA | *M. gordonae* type I, III, IV | 17 |
| GOR-II | AAAAACGTCGGCAAGCCGA | *M. gordonae* type II | 18 |
| SZU | AAATCTGAACGTCGGCGAG | *M. szulgai* | 19 |
| TER | AAAGCTCAGGACGGTCAGT | *M. terrae* | 20 |
| WT1 | AACCAGCTGAGCCAATTC | Wild Type 509–514 | 21 |
| WT2 | ATGGACCAGAACAACCCG | Wild Type 515–520 | 22 |
| WT3 | AAACTGTCGGGGTTGACC | Wild Type 521–525 | 23 |
| WT4 | TTGACCCACAAGCGCCGA | Wild Type 524–529 | 24 |
| WT5 | CTGTCGGCGCTGGGGC | Wild Type 530–534 | 25 |
| MT1 | CTGTTGGCGCTGGGGC | Mutant Type 531TTG | 26 |
| MT2 | AAAACCAACAAGCGCCGA | Mutant Type 526AAC | 27 |
| MT3 | AATGGTCCAGAACAACCCG | Mutant Type 516GTC | 28 |
| MT4 | AAAGCTGACCCCATTCAT | Mutant Type 513CCA | 29 |
| MT5 | AAAGCCGAGCCCATTCAT | Mutant Type 511CCG | 30 |

FIG. 3 shows the absence of bands in the reverse blot hybridization using the oligomer probes WT1–5. The failure of the probes to bind to their DNA recognition sequences indicates the presence of mutations in the region encoding susceptibility to rifampin. Therefore, the detection of said mutant types enables the determination of *M. tuberculosis* resistance to rifampin.

The oligomer probes in Table 1 were designed to hybridize at the same temperature and be highly specific for a particular species of *Mycobacterium*. To achieve these purposes, the length, GC content and positions of possible mismatch in the oligomer probes were modulated. For some less sensitive oligomer probes, non-specific nucleotides were added to the 5'-terminal ends in order to increase the efficiency of hybridization with the corresponding target DNA sequence.

Stable adhesion of the oligomer probes to the membrane is a result of a covalent linkage formed between an amino group conjugated to the 5'-terminal end of the oligomer probe and a carboxyl group on the membrane surface. These covalent links prevent the oligomer probes from moving freely on the membrane during the reverse blot hybridization. The present invention employs, but is not limited to, Biodyne-C membrane (Pall Biosupport, East Hills, N.Y.), a negatively charged nylon membrane, as any membranes with carboxyl groups on the surface may be preferably used.

In summary, the present invention provides primers for amplifying a 531bp fragment of the *M. tuberculosis* rpoB gene by PCR, the oligomer probes described in Table 1 and the membrane for adhesion to said oligomer probes, in order to specifically identify *M. tuberculosis* and MOTTs, and to detect mutations in the rpoB gene which confer drug resistance to the host *Mycobacterium*.

Further, the present invention provides a kit for the separate identification of *M. tuberculosis* and MOTTs, and for the detection of mutations in the rpoB gene which confers drug resisistance to the *Mycobacterium*, using said primers, the oligomer probes of Table 1 and the membrane for adhering said oligomer probes.

BRIEF DESCRIPTION OF THE DRAWINGS

FIG. 2 shows the nucleotide sequence (SEQ. ID. No. 31) of the 531bp fragment obtained by performing PCR amplification of the rpoB gene of *M. tuberculosis*.

Figure 1:
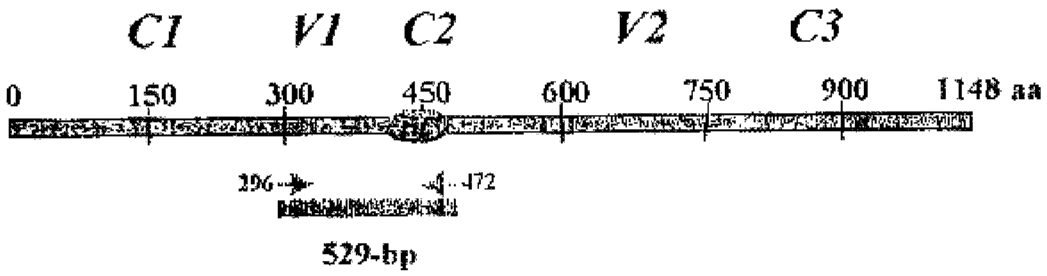
FIG. 1 is a genetic map of the *M. tuberculosis* rpoB gene.

The present invention will be explained in more detail with the following experimental examples. However, the present invention should not be limited to these examples, and it should be clearly understood that many variations and/or modifications of the basic inventive concepts herein taught which may appear to those skilled in the art will still fall within the spirit and scope of the present invention.

1. Mycobacterial Species

The species described in Table 2 below are used in the present experiments as standard species of *M. tuberculosis* and MOTTs. Rifampin susceptibility testing of clinically isolated *M. tuberculosis* was previously performed at the Korean Institute of Tuberculosis. Also, the identification of MOTTs was previously made using conventional microbiological and biochemical methods, such as the PCR-RFLP method developed by the present inventors.

TABLE 2

| | Species | Strain | Source |
|---|---|---|---|
| 1 | *M. abscessus* | Pettenkofer Inst. | YUMC |
| 2 | *M. africanum* | ATCC 25420 | KIT |
| 3 | *M. arcinogenes* | ATCC 35753 | KIT |
| 4 | *M. asiaticum* | ATCC 25276 | KIT |
| 5 | *M. aurum* | ATCC 23366 | KIT |
| 6 | *M. austroafricanum* | ATCC 33464 | KRIBB |
| 7 | *M. avium* | ATCC 25291 | KIT |
| 8 | *M. bovis* | ATCC 19210 | KIT |
| 9 | *M. bovis* BCG | French Strain 1173P2 | KIT |
| 10 | *M. celatum* type I/II | ATCC 51130/ ATCC 51131 | KIT |
| 11 | *M. chelonae* | ATCC 35749 | KIT |
| 12 | *M. chitae* | ATCC 19627 | KIT |
| 13 | *M. fallax* | ATCC 35219 | KIT |
| 14 | *M. fortuitum* type I/II | ATCC 6841/ ATCC 49404 | KIT |
| 15 | *M. gallinarum* | ATCC 19710 | KRIBB |
| 16 | *M. gastri* | ATCC 15754 | KIT |
| 17 | *M. genavense* | ATCC 51233 | KIT |
| 18 | *M. gilvum* | ATCC 43909 | KIT |
| 19 | *M. gordonae* type I-IV | ATCC 14470 | KIT |
| 20 | *M. haemophilum* | ATCC 29548 | KIT |
| 21 | *M. intracellulare* | ATCC 13950 | KIT |
| 22 | *M. interjectum* | ATCC 51457 | KIT |
| 23 | *M. intermedium* | ATCC 51848 | KIT |
| 24 | *M. kansasii* type I-V | | Pasteur |

TABLE 2-continued

| | Species | Strain | Source |
|---|---|---|---|
| | | | Inst. |
| 25 | *M. malmoense* | ATCC 29571 | KIT |
| 26 | *M. marinum* | ATCC 927 | KIT |
| 27 | *M. microti* | ATCC 19422 | KIT |
| 28 | *M. moriokaense* | ATCC 43059 | KRIBB |
| 29 | *M. mucogenicum* | ATCC 49650 | KIT |
| 30 | *M. neoaurum* | ATCC 25795 | KIT |
| 31 | *M. nonchromogenicum* | ATCC 19530 | KIT |
| 32 | *M. parafortuitum* | ATCC 19686 | KIT |
| 33 | *M. peregrinum* | ATCC 14467 | KIT |
| 34 | *M. phlei* | ATCC 11758 | KIT |
| 35 | *M. pulveris* | ATCC 35154 | KRIBB |
| 36 | *M. scrofulaceum* | ATCC 19981 | KIT |
| 37 | *M. smegmatis* | ATCC 19420 | KIT |
| 38 | *M. szulgai* | ATCC 35799 | KIT |
| 39 | *M. terrae* | ATCC 15755 | KIT |
| 40 | *M. thermoresistibile* | ATCC 19527 | KIT |
| 41 | *M. triviale* | ATCC 23292 | KIT |
| 42 | *M. tuberculosis* H37Rv | ATCC 27294 | KIT |
| 43 | *M. ulcerans* | ATCC 19423 | KIT |
| 44 | *M. vaccae* | ATCC 15483 | KIT |
| 45 | *M. xenopi* | ATCC 19250 | KIT |

2. Isolation of DNA

Genomic DNA from the mycobacterial species described in Table 2 was obtained by boiling 0.4 mL mycobacterial suspensions. About 5 uL of genomic DNA was used in each PCR amplification.

For patient-derived clinical samples, DNA was isolated from patients' expectoration. The expectoration was treated with an equal volume of 4% NaOH and then the solution was homogenized by vortexing, followed by reaction at room temperature for 15 minutes. Distilled water was added to the reaction solution to a final volume of 50 mL. The solution was spun at 3,000 rpm for 20 minutes, and the supernatant was discarded. The pellet was resuspended and 500 uL of the solution was mixed with an equal volume of 2% NaOH. Next, the solution was boiled for 2 minutes and then spun at 12,000 rpm for 3 minutes, followed by discarding the supernatant. The pellet was resuspended in 1 mL of 0.1M Tris-Cl (pH 6.8), mixed well, spun at 12,000 rpm for 3 minutes, and the supernatant was discarded. Glass beads were added to the pellet and the solution was shaken for 90 seconds. Approximately 5–10 uL of the DNA was used in the following PCR amplification.

3. PCR Amplification

PCR reaction mixtures contained 50 mM KCl, 10 mM Tris-HCl (pH 8.3), 1.5 mM $MgCl_2$, 0.001% gelatin (w/v), dNTPs (each 200 $\mu$M), Taq polymerase (1.25 unit), primers (10 pmol) and genomic DNA (50–100 ng) at a final volume of 50 uL. The PCR reaction was performed under the following conditions: denaturation for 5 minutes at 95° C.; 35 cycles of denaturation at 94° C. for 30 sec, followed by annealing at 58° C. for 30 sec, followed by extension at 72° C. for 45 sec; and finally, 10 minutes of extension at 72° C. The sequences of the primers employed in the PCR reactions are as follows: MOTT-rpo-long-B-5':5'-TCAAGGAGAAGCGCTACGACCTGGC-3' (SEQ ID NO. 1) TR8-long-NB-3':5'-ACGGGTGCACGTCGCGGACCTCCA-3' (SEQ ID NO. 2) and the region of the rpoB gene amplified by this PCR reaction is shown in FIG. 1. Further, the sequence of the 531bp PCR fragment is shown in FIG. 2.

Confirmation of the 531bp PCR product was obtained by electrophoresis of about 5 uL of the reaction solution on a 1.0% agarose gel.

4. Oligomer Probes

The oligomer probes used to separately identify *M. tuberculosis* and specific MOTTs, and the oligomer probes used to detect mutations in the DNA sequence which encode rifampin susceptibility in *M. tuberculosis*, were designed using the rpoB gene sequence of each specific *Mycobacterium* species, respectively. Each oligomer probe was capable of hybridizing with its target DNA sequence at the same temperature. Also, the sequence length and GC content of each oligomer probe was adjusted to increase the specificity and sensitivity to its target DNA sequence. In particular, for oligomer probes which exhibited lower sensitivity to their target sequences, non-specific nucleotides were added to the 5'-terminal end in order to increase the efficiency of binding of oligomer probe to the target DNA sequence. The DNA sequences of said oligomer probes are presented in Table 1.

Stable adhesion of the oligomer probes to the Biodyne-C membranes was facilitated by the formation of covalent bonds between amino groups conjugated to the 5'-terminal ends of the oligomer probes and carboxyl groups on the surface of the membranes.

5. PCR-Reverse Blot Hybridization

After PCR amplification, the 531bp PCR product was confirmed on an agarose gel. PCR-reverse blot hybridization was performed using 10 uL of the confirmed PCR product and oligomer probes adhered to a Biodyne-C membrane as prepared above. The oligomer probes and PCR product were loaded using a Miniblotter-MN45 (Immunetics, Cambridge, Mass.).

Briefly, PCR-reverse blot hybridization was performed as follows. The confirmed PCR product (10 uL) was diluted by adding 150 uL of 2×SSPE/0.1% SDS solution. Next, the diluted PCR product was denaturated at 99° C. for 10 minutes, followed by cooling in ice. Before loading the PCR product on the membrane, the Biodyne-C membrane was soaked in 100 mL of 2×SSPE/0.1% SDS solution at room temperature for 5 minutes and then positioned on the support cushion in the Miniblotter. After aspirating the remaining moisture in the slot, the diluted PCR product was loaded into the slot, with the slot vertically positioned in the direction of the adhered oligomer probes. The empty slot next to the slot loaded with PCR product was filled with 2×SSPE/0.1% SDS in order to prevent cross-flow. The hybridization reaction was performed in a 50° C. flat-ground incubator for 2 hours. For preventing cross-flows between neighboring slots, the membrane was not shaken.

Following hybridization, the sample was removed from the Miniblotter using an aspirator. The membrane was removed from the Miniblotter and washed two times with 100 mL of 2×SSPE/0.5% SDS solution at 57° C. for 10 minutes. Then, the membrane was put in a rolling bottle, and 10 mL of streptavidine-alkaline phosphatase conjugate solution diluted 1:2000 with 2×SSPE/0.5% SDS solution was poured into the membrane, followed by reaction at 42° C. for 60 minutes. Then, the membrane was washed two times with 100 mL of 2×SSPE/0.5% SDS solution at 42° C. for 10 minutes, and two times with 100 mL of 2×SSPE solution for 5 minutes.

For chemiluminescent detection of the hybridized reaction products, the membrane was treated with 10 mL of CDP-Star™ dectection reagent (Amersham Pharmacia Biotech., Buckinghamshire, England) for 4 minutes. Next, the membrane was wrapped with overhead sheet or wrap and exposed to X-ray film for 30 minutes (if needed, further exposure to X-ray film for up to 2 hours), thereby yielding the experimental results described in the following section.

5. Results

1) PCR Amplification of the rpoB Gene from Standard Species of *Mycobacterium*

Figure 4:
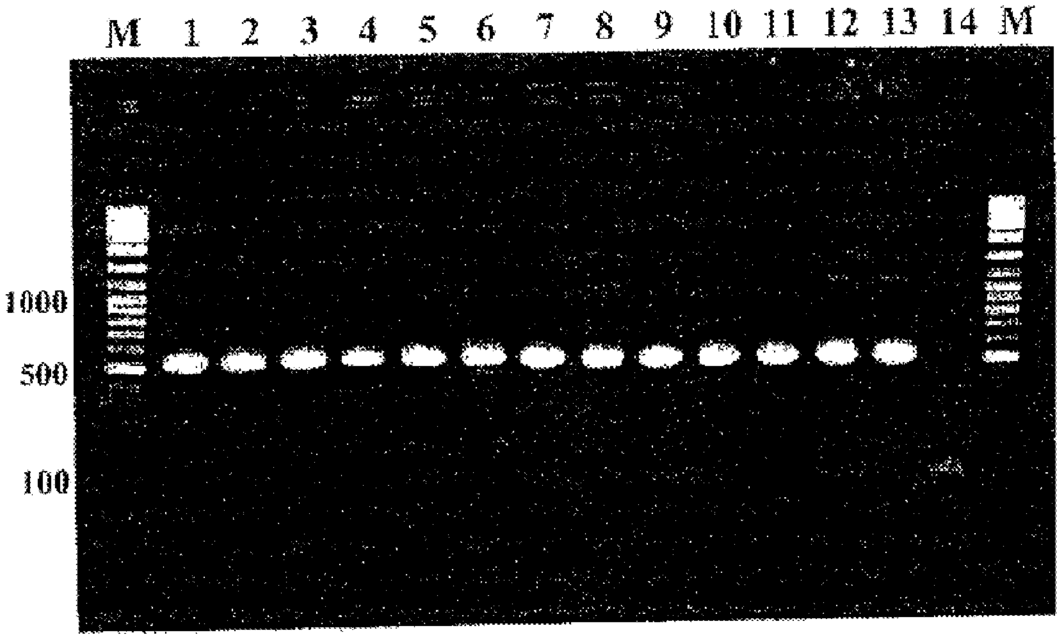
FIG. 4 is a drawing showing the 531bp fragment of the rpoB gene amplified by PCR using DNA isolated from standard mycobacterial species and the primers described by SEQ. ID. NOs. 1 and 2. The lane "M" is the Gene Ruler™ DNA size marker, lanes 1–13 show PCR products amplified from standard species of *M. tuberculosis, M. avium, M. intracellulare, M. scrofulaceum, M. szulgai, M. gordonae, M. kansasii, M. abscessus, M. chelonae, M. gastri, M. fortuitum, M. ulcerans*, and *M. terrae,* respectively, and lane 14 is a negative control for PCR amplification.

DNA was isolated from 54 standard species of *Mycobacterium* (furnished by ATCC), including subtypes kept in the Korean Institute of Tuberculosis. The rpoB gene regions were amplified from the samples by PCR as described previously. As shown in FIG. 4, 531bp PCR fragments, which include the DNA sequence used for separately identifying *M. tuberculosis* and MOTTS and the DNA sequence that encodes for resistance to antituberculosis drugs, were amplified using the primers MOTT-rpo-long-B-5' and TR8-long-NB-3', irrespective of species type (see, FIG. 1).

2) PCR-Reverse Blot Hybridization Using Amplified rpoB Gene Products from Standard Species of *Mycobacterium*

Figure 5:
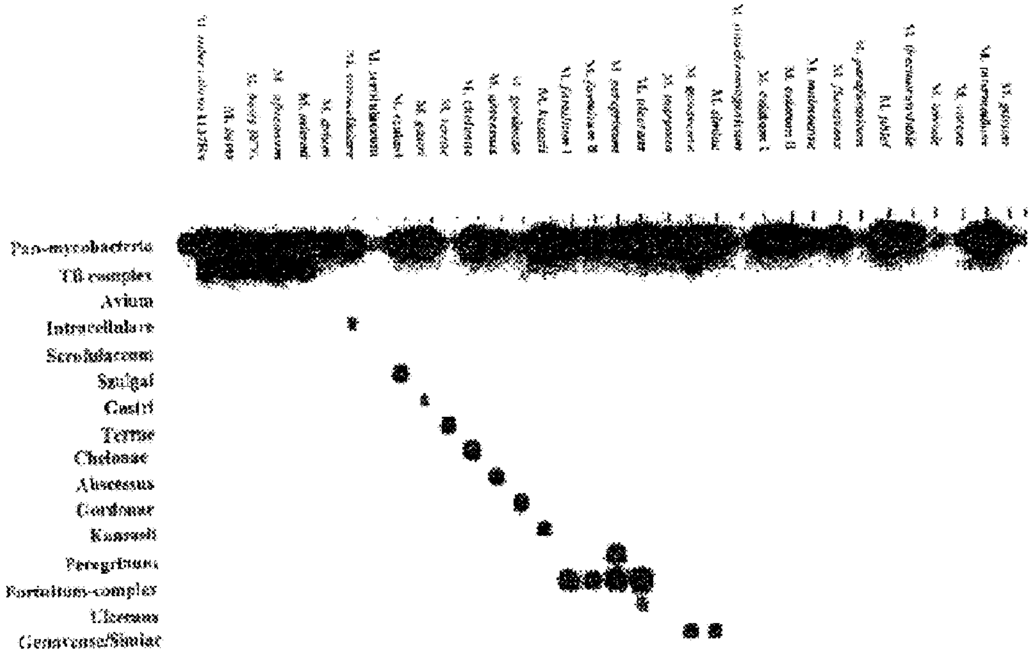
FIG. 5 is a drawing showing results of a PCR reverse blot hybridization of the present invention for standard species of *M. tuberculosis* and MOTTs, wherein PCR products amplified from each mycobacterial species are hybridized with the corresponding species-specific oligomer probes.

The PCR product amplified from genomic DNA isolated from each standard species of *Mycobacterium* was hybridized specifically with the oligomer probe that was designed for that species, thereby confirming the separate identification of each mycobacterial species. The results are shown in FIG. 5. Most of the standard mycobacterial species bound to the oligomer probe designed to target all *Mycobacterium* (SEQ ID NO. 3, Table 1), and all the species-specific oligomer probes bound to the PCR products to which they were designed to have specificity for. These results indicate that the oligomer probes according to the present invention may be used to separately identify *M. tuberculosis* and MOTTs. Moreover, the species-specific oligomer probes did not hybridize with PCR products amplified from mycobacterial species that they were not designed to have specificity for.

As exemplified by *M. gordonae, M. kansasii* and *M. fortuitum* in FIG. 5, the same species may have different subtypes which share some sequence polymorphism. Therefore, the oligomer probes of the present invention were designed to hybridize with as many subtypes of the same species as possible. Although DNA isolated from *M. terrae* did not hybridize with the oligomer probe that targets all *Mycobacterium*, it did specifically hybridize with the oligomer probe specific to *M. terrae*. Moreover, although the DNA isolated from *M. genavense* hybridized with the oligomer probe specific to *M. tuberculosis*, it also hybridized specifically with the oligomer probe specific to *M. genavense*.

3) PCR-Reverse Blot Hybridization Using Amplified rpoB Gene Products from Clinical *Mycobacterium* Species Isolated at the Korean Institute of Tuberculosis The identification of clinical mycobacterial species was performed using PCR-reverse blot hybridization as described previously. Clinical mycobacterial species were previously identified by microbiological, biochemical, and molecular biological methods such as PCR-RFLP. These identified mycobacterial species include *M. tuberculosis* and MOTTs with clinical significance or with high frequency of appearance. Examples of such MOTTs include pathogenic species such as *M. avium-intacellulare* complex, *M. kansasii, M. marinum, M. fortuitum, M. chelonae*, and *M. abscessus*; pathogenic MOTTs with less frequency of appearance include *M. malmoense, M. asiaticum, M. xenopi, M. simiae, M. scroflaceum, M. nonchromogenicum, M. peregrinum, M. szulgai, M. haemophilum,* and *M. ulcerans*; and, non-pathogenic MOTTs with high frequency of appearance include *M. terrae* and *M. gordonae*. Among these, MOTTs that are generally available at the Korean Institute of Tuberculosis include *M. avium, M. intracellulare, M. fortuitum, M. terrae, M. gordonae, M. chelonae,* and *M. abscessus*.

Figure 6:
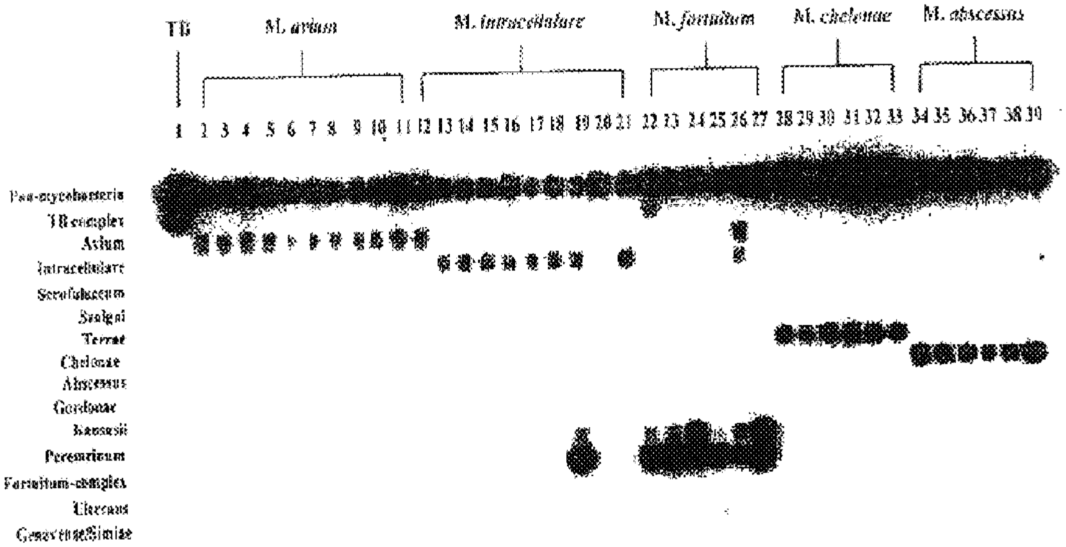
FIG. 6 is a drawing showing results of a PCR reverse blot hybridization of the present invention for clinically isolated MOTTs.

PCR-reverse blot hybridization was performed with MOTTs species with a high frequency of appearance in Korea. As shown in FIG. 6, each clinical mycobacterial species hybridized to the oligomer probe to which it had specificity for. Identification of Mycobacterial species using the method of the present invention confirmed the results obtained by previous microbiological, biochemical and molecular biological methods. Further, using the method of the present invention, it was confirmed that various species of MOTTs exist in mixed populations. This result was not previously obtained with microbiological and biochemical analyses, such as PCR-RFLP.

Figure 3:
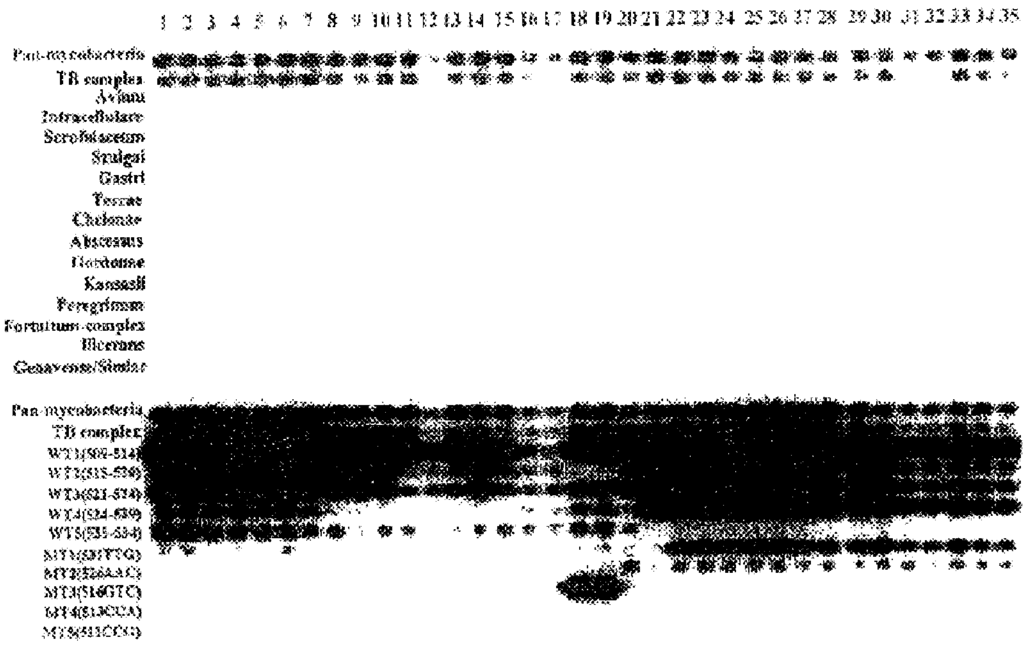
FIG. 3 is a drawing showing results of a PCR reverse blot hybridization of the present invention used to identify *M. tuberculosis* and MOTTS, and to detect mutations in the amplified segments of the *M. tuberculosis* rpoB gene, for the determination of susceptibility to rifampin. Lanes 1–6 represent *M. tuberculosis* with a wild type rpoB gene and therefore retaining susceptibility to rifampin; lane 7 represents *M. tuberculosis* with a mutation in the 514–520 nucleotide region that confers resistance to rifampin; lanes 8–15 represent rifampin-resistant *M. tuberculosis* with a mutation in the 524–529 nucleotide region; lane 16 represents rifampin-resistant *M. tuberculosis* with a mutation of nucleotide 511 to CCG; lane 17 represents rifampin-resistant *M. tuberculosis* with a mutation of nucleotide 513 to CCA; lanes 18–19 represent rifampin-resistant *M. tuberculosis* with a mutation of nucleotide 516 to GTC; lane 20 represents rifampin-resistant *M. tuberculosis* with a mutation of nucleotide 526 to AAC; lane 21 represents rifampin-resistant *M. tuberculosis* with a mutation of nucleotide 531 to TGC; and lanes 22–35 represent rifampin-resistant *M. tuberculosis* with a mutation of nucleotide 531 to TTG.

4) Identification of *M. tuberculosis* and Determination of Susceptibility to Rifampin In order to determine the rifampin susceptibility of an identified sample of *M. tuberculosis*, PCR-amplified segments of both the wild type and mutated rpoB gene were hybridized with oligomer probes which target specific mutations in the gene which confer resistance to rifampin, using the PCR-reverse blot hybridization method and oligomer probes described previously. As shown in FIG. 3, PCR-amplified sequences with specific mutations that confer rifampin resistance to *M. tuberculosis* were detected and distinguished from the wild type DNA sequence using the oligomer probes and method of the present invention.

Figure 7:
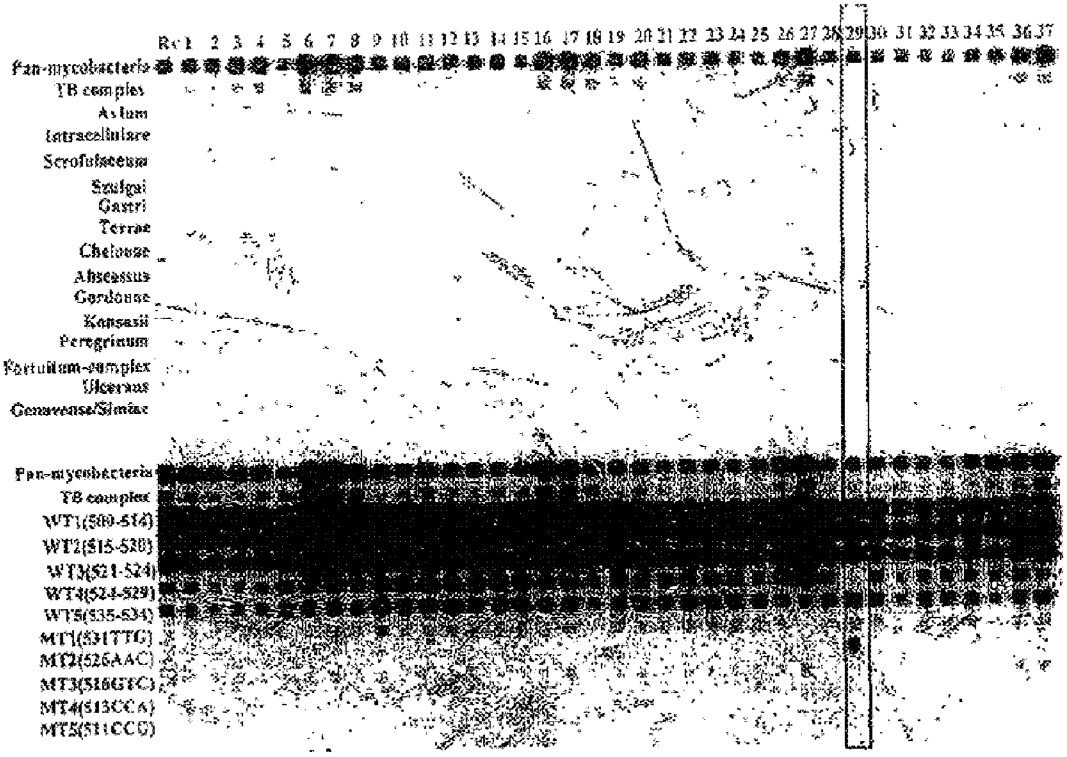
FIG. 7 is a drawing showing results of a PCR reverse blot hybridization used to separately identify *M. tuberculosis* and MOTTS, and to detect mutations in the amplified rpoB gene segments of thirty-seven clinical samples of *mycobacterium*.

5) Identification of *Mycobacterium* and Determination of Drug Susceptibility to Rifampin Using DNA Isolated from Patient Expectoration Samples DNA was isolated from expectoration samples of thirty-seven patients diagnosed as smear positive by acid fast staining (Laboratory services in Tuberculosis control, Part II. Microscopy, Global Tuberculosis Programme, World Health Organization 1998). The rpoB gene region was amplified by PCR using the isolated DNA and the amplified PCR products were subjected to PCR-reverse blot hybridization as described previously, in order to identify the species of *mycobacterium* and to determine the drug susceptibility of identifed *M. tuberculosis* samples to rifampin. As a result, the mycobacteria in smear positive expectoration samples were separately identified as *M. tuberculosis* or MOTTs. The mycobacteria identified as *M. tuberculosis* were subsequently determined to be either rifampin-susceptible or rifampin-resistant, based on detection of drug-resistant genotypes using rpoB gene mutation-specific oligomer probes. As shown in FIG. 7, *M. tuberculosis* was identified in all the samples; the sample in lane 29 in particular was determined to be rifampin-resistant *M. tuberculosis*.

In summary, the method according to the present invention may be used to separately identify *M. tuberculosis* and MOTTs and, for species identified as *M. tuberculosis*, lead to the determination of resistance to antituberculosis drugs such as rifampin by the detection of nucleotide mutations in the rpoB gene. The present invention reduces the time required for *Mycobacterium* identification and determination of drug resistance to a total of 1–2 weeks, compared to conventional methods which require a total of 3–4 weeks. Further, the method of the present invention does not expose experimenters to extensive contact with harmful mycobacteria while providing the means to obtain rapid and accurate results.

REFERENCES

1. Kox L F F, van Leeuwen J, Knijper S, Jansen H M and Kolk A H J: PCR assay based on DNA coding for 16S rRNA for detection and identification of Mycobacteria in clinical samples. *J Clin Microbiol* 33: 3225–3233, 1995.

2. Sanguinetti M, Posteraro B, Ardito F, Zanetti S, Cingolani A, Sechi L, de Luca A, Ortona L and Fadda G: Routine use of PCR-reverse cross-blot hybridization assay for rapid identification of *Mycobacterium* species growing in liquid media. *J Clin Microbiol* 36: 1530–1533, 1998.
3. Garcia, M. J. and E. Tabares: Separation of *Mycobacterium gadium* from the rapidly growing mycobacteria on the basis of DNA homology and restriction endonuclease analysis. *J. Gen. Microbiol.* 132: 2265–2269, 1986.
4. Rubina, P., J. T. Kuach, and P. Mounts: Isolation and restriction endonuclease analysis of mycobacterial DNA. *J. Gen. Microbiol.* 132: 541–551, 1986.
5. Bai, G H.: Rapid identification of *Mycobacterium avium* and *Mycobacterium intracellulare* by the amplification of rRNA sequences. *J. Kor. Soc. MIcro.* 27(5): 443–448, 1992.
6. Lee, H., H. Park, S. Cho, G Bai and S. Kim. 2000. Species identification of Mycobacteria by PCR-Restriction Fragment Length Polymorphism of the rpoB gene. J. Clin. Microbiol. 38:2966–2971.
7. Kamerbeek, J., Schouls, A. Kolk, M. van Agterveld, D. van Soolingen, S. Kuijper, A. Bunschoten, H. Molhuizen, R. Shaw, M. Goyal, and J. van Embden. 1997. Simultaneous detection and strain differentiation of *Mycobacterium tuberculosis* for diagnosis and epidemiology. J. Clin. Microbiol. 35:907–914.
8. Woods, G. L. and T. A. Washington II: Mycobacteria other than *Mycobacterium tuberculosis*: Review of microbiologic and clinical aspects. Rev. Inf. Dis. 9(2): 275–294, 1987.
9. Jenkins, P. A.: Mycobacteria in the environment. *J. Appl. Bact. Sym. Suppl.* 70: 1375–1415, 1991.
10. Tsukamura, M., H. Shimoide, A. Kuse: Epidemologic studies of lung disease due to mycobacteria other than *Mycobacterium tuberculosis* in Japan. *Rev. Inf Dis.* 3(5): 997–1007, 1981.
11. O'Brien, R. J., Geiter, L. J., and Snider, D. E. : The epidemiology of nontuberculous mycobacterial diseases in the United States. Results from a national survey. *Am. Tev. Respir. Dis.* 135: 1007–1014, 1987.
12. Bai, G. H., Park, K. S., and Kim, S. J. : Clinically isolated mycobacteria other than *Mycobacterium tuberculosis* from 1980 to 1990 in Korea. *J. Kor. Soc. Micro.* 28(1):1–5, 1993.

What is claimed is:

1. A method for identifying *Mycobacterium tuberculosis* and non-tuberculosis *Mycobacterium* (MOTT) which comprises the following steps:

(1) isolating DNA from a sample;

(2) amplifying a 531 bp fragment of the rpoB gene by PCR using said DNA isolated in the above step (1) and the primers of SEQ. ID. NOs. 1 and 2;

(3) performing PCR-reverse blot hybridization by hybridizing the PCR product obtained in the above step (2) with one or more oligomer probes, said oligomer probes selected from the group of oligomer probes consisting of SEQ. ID. NOs. 5, 6, 9, 10, 13 and 14, adhered to a suitable membrane.

2. The method of claim 1, wherein said suitable membrane is a negatively-charged nylon membrane.

3. The method of claim 2, wherein said negatively-charged nylon membrane has surface carboxyl groups.

4. A pair of oligonucleotide primers consisting of the DNA sequences described by SEQ. ID. NOs. 1 and 2, respectively.

5. An oligomer probe selected from the group consisting of SEQ. ID. NOs. 5, 6, 9, 10, 13 and 14, wherein said probe can be used to hybridize to a PCR-amplified fragment of the mycobacterial rpoB gene in order to separately identify *Mycobacterium tuberculosis* and MOTTs.

6. A kit for separately identifying *Mycobacterium tuberculosis* and MOTTs, which comprises (1) a pair of oligonucleotide primers described by SEQ. ID. NOs. 1 and 2 and (2) one or more oligomer probes selected from the group consisting of SEQ. ID. NOs. 5, 6, 9, 10, 13 and 14.

* * * * *